United States Patent [19]
Houben

[11] Patent Number: 5,817,133
[45] Date of Patent: Oct. 6, 1998

[54] PACEMAKER WITH MORPHOLOGICAL FILTERING OF SENSED CARDIAC SIGNALS

[75] Inventor: Richard P. M. Houben, Berg En Terblijt, Netherlands

[73] Assignee: Medtronic, Inc., Minneapolis, Minn.

[21] Appl. No.: 811,053

[22] Filed: Mar. 4, 1997

[51] Int. Cl.$^6$ ................................................ A61N 1/362
[52] U.S. Cl. ............................................................ 607/9
[58] Field of Search .............................. 607/9, 5, 17, 25, 607/26, 27

[56] References Cited

U.S. PATENT DOCUMENTS

| | | |
|---|---|---|
| 4,721,114 | 1/1988 | DuFault et al. . |
| 5,086,772 | 2/1992 | Larnard et al. . |
| 5,170,193 | 12/1992 | McMillan et al. . |
| 5,193,550 | 3/1993 | Duffin . |
| 5,240,009 | 8/1993 | Williams . |
| 5,336,880 | 8/1994 | Leclerc et al. . |
| 5,351,696 | 10/1994 | Riff et al. . |
| 5,436,984 | 7/1995 | Sarkkinen et al. . |

FOREIGN PATENT DOCUMENTS

WO95/10086  4/1995  United Kingdom .

OTHER PUBLICATIONS

"Impulse Noise Suppression and Background Normalization of Electrocardiogram Signals Using Morphological Operators" Chu, et al. IEEE Transactions on Biomedical Engineering, vol. 36, No. 2, Feb. 1989.

"An Approach to QRS Complex Detection Using Mathematical Morphology" Trahanias, PE, IEEE Transactions on Biomedical Engineering, vol. 40., No. 2, Feb. 1993.

*Primary Examiner*—Scott M. Getzow
*Attorney, Agent, or Firm*—Michael J. Jaro; Harold Patton

[57] ABSTRACT

A system and method are provided, particularly useful for an implantable cardiac pacemaker, for morphological filtering of sensed signals to reliably and accurately identify one or more specified wave portions of the sensed signals. In a first pacemaker embodiment, morphological filtering is done on the sensed atrial signal, whereby the P-wave peak is discriminated out, with the resulting signal minus the P-wave peak being then subtracted from the inputted atrial signal to provide the atrial peak, thereby effectively eliminating sensing of FFR-wave portions. By setting the morphological filter length to correspond to about the duration of the P-wave peak, or just slightly larger, and by adjusting sampling frequency to correspond to cardiac rate variations, there is provided optimized filtering consistent with low power consumption in an implantable device. In other embodiments, FFR-waves, T-waves, VT, SVT and sinus tachycardia are identified by using templates matched to the wave to be identified. The invention can be performed with either analog or digital embodiments, analog embodiments providing for lower power consumption.

42 Claims, 9 Drawing Sheets

PACEMAKER WITH MORPHOLOGICAL FILTERING OF SENSED CARDIAC SIGNALS

FIELD OF THE INVENTION

This invention relates to cardiac pacemakers and other medical devices and, more specifically, apparatus and methods for use in cardiac pacemakers in filtering sensed signals, and more particularly filtering sensed cardiac signals.

BACKGROUND OF THE INVENTION

In many medical device applications, such as cardiac pacemakers, there is a great need for accurate detection of sensed signals, and in particular a need for discriminating or separating out certain portions of sensed signals. For example, dual chamber pacemakers sense spontaneous P-waves from the patient's atrium, in order to determine whether or not to pace the atrium and/or for timing out a synchronous ventricular pace pulse. In many such applications, filtering on the basis of frequency is inadequate, because of the overlap of frequencies in signal portions to be accepted and signal portions to be rejected. Specifically, in a cardiac pacemaker which senses the atrial electrogram (AEGM), it is difficult to separate out the far field R-wave (FFR-wave) from the desired P-wave portion of the signal, due to the overlap of frequencies in the two different signal portions. In processing sensor signals or other sensed physiological signals, the use of frequency response filters, or even switchable frequency response filters, often cannot solve the problem for certain signals and rhythms.

Many different schemes have been proposed for addressing this problem. For example, for the task of screening out the FFR-wave from the atrial signal, various techniques such as sensitivity adjustment, "window" tracking so as to detect at about the time of the expected signal, etc. have been implemented. In addition to linear high pass filters, other approaches to the problem have adaptive finite impulse response filters (AFIR) and the use of hidden Markov models. However, these approaches have not led to significant acceptance in the pacing environment. The best possible solution remains an approved filter which effectively distinguishes the desired wave portion from the undesired portion or portions.

There thus is presented a continuing and substantial problem, particularized for implantable pacemakers, for providing efficient and unambiguous recognition of different wave portions of a sensed cardiac signal, e.g., QRS, T and P-wave portions; and also a need to adapt the filtering capability to different rates, in order to detect the desired signal portions during specific arrhythmias such as ventricular fibrillation (VF), ventricular tachycardia (VT), sinus tachycardia (ST) and super-ventricular-tachycardia (SVT). Further, due to power limitations in implantable devices, there is a need to achieve the needed improvement while minimizing the hardware and the processing involved.

The approach taken in this invention is based on the recognition that even where the frequency spectra of different wave portions overlap, the shapes of the respective wave portions are distinct. Thus, the far field R (FFR) wave, while it has many of the same spectral components as the QRS, is relatively stretched out, or wider in form, due to the propagation of the signal from the ventricle into the atrial chamber where it is sensed by atrial electrodes. This suggests the use of morphological filtering techniques in filtering and detecting the P-wave and filtering out the FFR-wave. Morphological-type filters have been widely used in image processing, but are relatively new in signal processing. This invention is based on adaptation of morphological filtering in real time signal processing of analog signals for use by pacemakers and other implantable medical devices.

SUMMARY OF THE INVENTION

It is an object of this invention to provide new filtering techniques for use in devices such as cardiac pacemakers, and specifically the use of morphological-type filters for reliable discrimination of desired wave portions and rejection of undesired wave portions. For example, in a preferred embodiment of this invention, morphological filtering is used to operate on the sensed atrial signal, or AEGM, so as to reliably detect P-waves while rejecting FFR-wave portions. For this application, the invention provides the P-wave clearly separated out, and with a substantially zero base line.

In a preferred pacemaker embodiment of this invention, the sensed atrial signal from the patient is sampled to get the sampled signal. The sampled signal is passed through a morphological filter, either an analog or digital embodiment. The morphological filter operates on the signal by analyzing successive sets of samples selected to approximate the width of the P-wave, thereby filtering out the P-wave but leaving signal portions lacking a morphological fit, such as the FFR-wave. The signal that has been thus morphologically filtered to suppress the P-wave peak is then subtracted from the sampled signal, leaving the P-wave portion that was morphologically filtered out, and thereby rejecting the wider FFR-wave. While the morphological filter may have an analog, digital optical or hybrid-type embodiment, analog is presently preferred for the pacemaker environment because of lower power requirements. The filter is set to operate on about 5–10 samples at a time, with a sample rate around 1 kHz, for optimum P-wave detection. The filter is preferably open-close for best operation on P-wave peaks, but may also incorporate just the open operation. The template, which is adjustable and/or programmable, is suitably common to both open and close operations, and may use zeros for a majority of the adding or subtracting operations, for circuit simplicity.

In yet another embodiment, plural wave portions of incoming signals, e.g., P-waves and T waves in a pacemaker, can be morphologically operated on with the same template configuration. Thus, FFR-waves, T-waves, QRS-waves and P-waves can be morphologically identified; and different types of tachycardia can be discriminated. Further, the sampling rate is suitably adjusted as a function of detected R-R rate, to optimize morphological filtering of signals that vary widely in frequency, thereby enabling improved tracking of arrhythmias such as ventricular tachycardia (VT) and ventricular fibrillation (VF).

DETAILED DESCRIPTION OF THE PREFERRED EMBODIMENTS

Figure 1A:
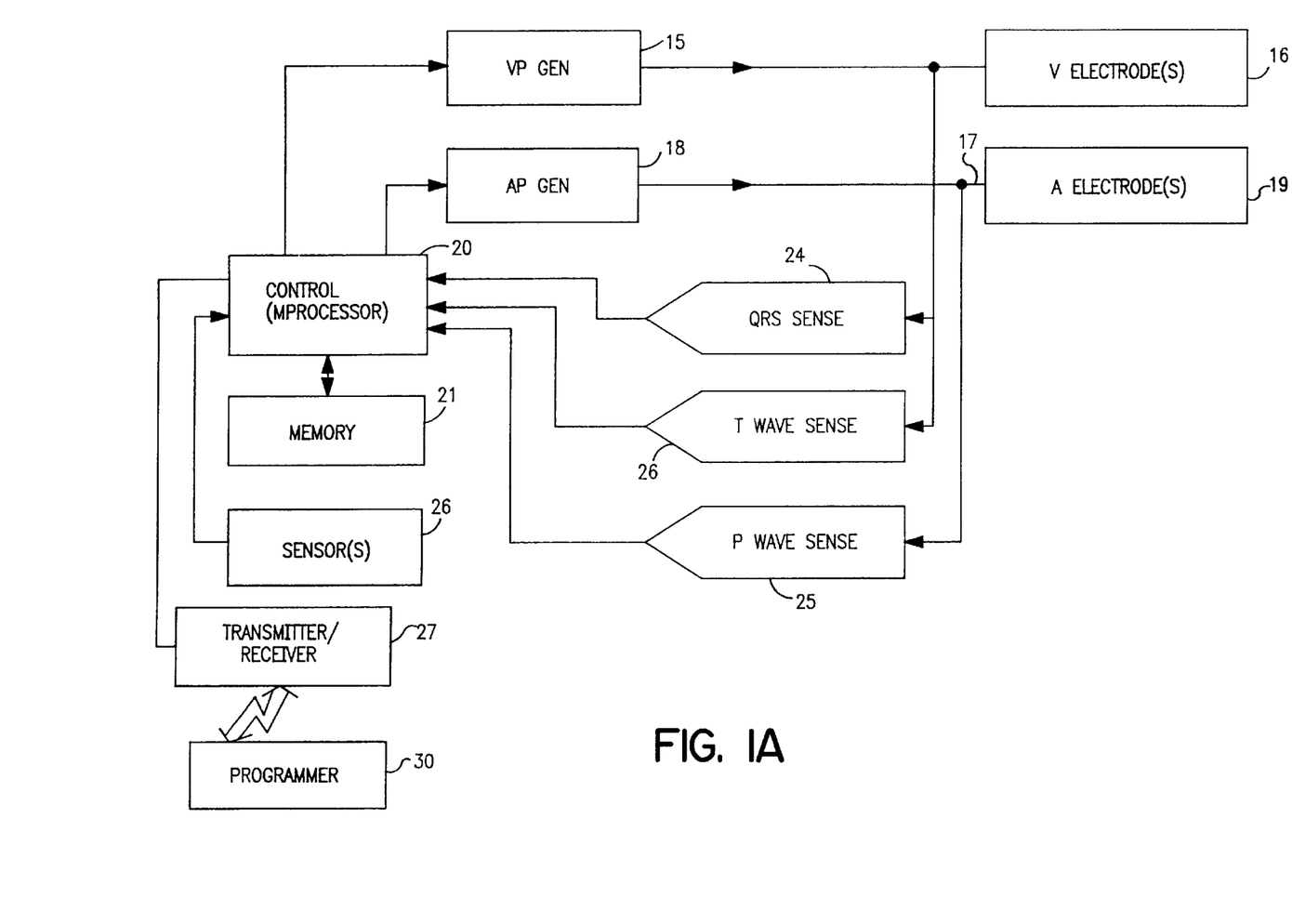
FIG. 1A is a block diagram illustrating the primary components of an implantable cardiac pacemaker in accordance with this invention.

Referring now to FIG. 1A, there is shown a simplified block diagram of the primary components of a pacemaker as can be used in the system and method of this invention. Although a dual chamber pacemaker is illustrated for completeness, it is to be understood that the invention is applicable to single or dual chamber rate responsive pacemakers. A ventricular pace generator is illustrated at 15 for generating and delivering ventricular pace pulses under control of control unit 20, in a known fashion. The ventricular pace pulses are delivered to one or more ventricular electrodes illustrated at 16. Likewise an atrial pace generator is illustrated at 18, which generates atrial pace pulses under control block 20 and delivers the atrial pace pulses to one or more atrial electrodes as illustrated at 19. Sense signals from the ventricular electrode or electrodes are connected to QRS sense amplifier 24 and T-wave sense amplifier 26, the outputs of which are inputted to control block 20 for processing. Likewise, signals detected in the atrium by electrodes 19 are delivered to P-wave sense amplifier 25, the output of which is connected through to control 20.

Control block 20 suitably incorporates a microprocessor with associated software, the software being stored in memory 21, as indicated. Memory 21 may contain RAM and ROM, and the assignment of pacemaker functions can be divided between hardware and software in any desired manner. One or more sensors 26 may be provided to continuously detect rate-indicating parameters, the parameter signals being inputted to control block 24 to provide rate responsive control, in a known manner. Alternately, the rate responsive parameter is QT interval, which is determined by control 20 by timing the duration between a delivered stimulus (VP) and the following T wave. As illustrated at 27, the pacemaker suitably has a transmitter/receiver for receiving programmer communications from an external programmer 30, and for down loading collected data back to the programmer, in a known fashion.

For the preferred analog embodiment of this invention, the morphological filter or filters are part of the circuitry of block 24–26, under control of control circuit 20. For a digital embodiment, the morphological operations are carried out by the microprocessor of block 20.

Figure 1B:
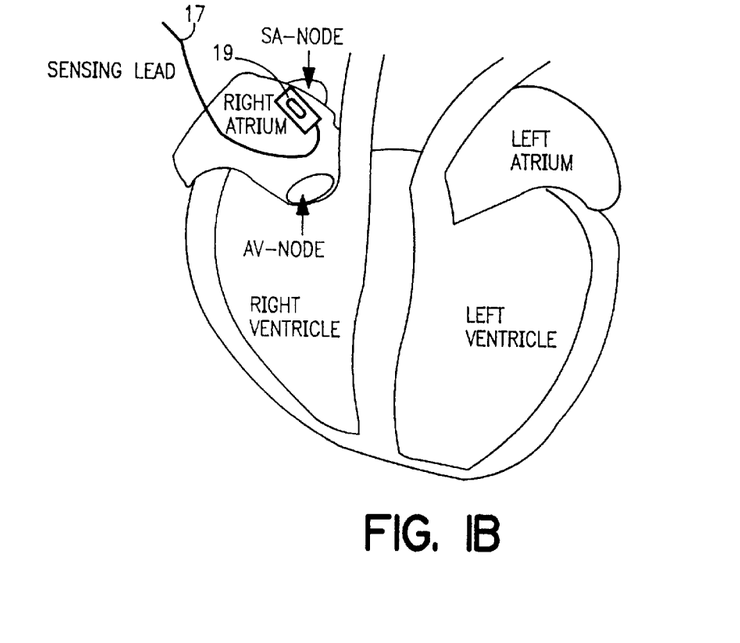
FIG. 1B is an illustration showing an atrial lead with an atrial electrode positioned in the patient's right atrium, for sensing the AEGM to be operated on in accordance with the principles of this invention.
Figure 2:
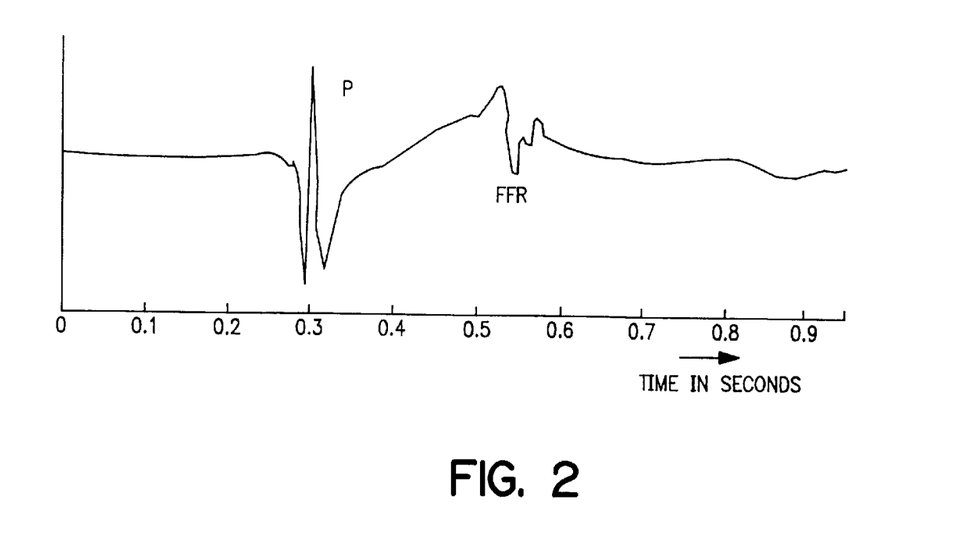
FIG. 2 is a diagram illustrating an AEGM which has not only a P-wave portion but a pronounced FFR-wave portion.

Referring now to FIG. 1B, there is shown a diagrammatic representation of the chambers of the heart, with an atrial lead 17 inserted into the right atrium so that atrial electrode 19 is positioned within the right atrium. The signal generated by the sino-atrial node is captured by the electrode (or electrodes in a bipolar system), for purposes of providing P-wave information. As is known, the P-wave is extremely important for dual chamber pacemakers, e.g., DDD or VDD, as the timing of the P-wave enables the pacemaker to time out and deliver a synchronous ventricular pace pulse. Also, the P-wave is used in atrial pacemakers, e.g., AAI, or in a DDD pacemaker, to determine whether or not to stimulate the atrium. Referring to FIG. 2, there is shown a typical AEGM captured by an atrial sensing lead. As is known, the pulse generated by the SA-node depolarizes through the atrial chambers and causes the atrial muscles to contract and pump blood into the ventricular chambers. This pulse is referred to as the P-wave, and is represented by the complex indicated by the letter P in FIG. 2. The P-wave is delayed by the AV-node for about 200 ms, after which the propagation of the wave generates the QRS complex in the ventricular chambers. The QRS complex makes the ventricular muscles contract and pump the blood from the ventricles into the arteries. The magnitude of the QRS complex is much greater than that of the P-wave, such that even though the atrial sensing electrode is placed as close as possible to the AV node, a substantial R-peak from the ventricle still appears in this signal. This appearance of the R-peak is referred to as the far field R-wave (FFR), and when sensed in the atrium is clearly a disturbance. However, as stated above, the FFR-wave is hard to discriminate from the P-wave by simply using linear filters, because of the similarity of the power spectral densities of typical P-and FFR-waves.

The morphological filters used in the practice of this invention are constructed from a combination of a morphological operators. Morphological operators use a separate data set to transform a set of input samples to a set of output samples. The set, known as the structuring element (or simply "template") defines the operation that takes place. As seen in connection with FIGS. 3A and 3B, the degree of complexity of morphological filters is relatively low, because only delay lines, additions, subtractions, and maximum- and minimum functions are used.

There are two morphological operations, namely dilation and erosion. Although these operations appear in tandem, they are defined separately. The dilation of a signal X, of length n samples, by a template m, with a template length M, producing an output is defined as $$Yd_n = D(X_n) = \text{MAX}_{i=0\ldots M-1}\{X_{n-i}+m_i\} M-1 \leq n \leq N-1$$

As can be seen, dilation is an expanding operator, meaning that the outputs are always greater than the corresponding inputs, if the template $m_i$ is greater than zero for all i. The $X_{n-i}$ term looks back in time, and once the first M−1 samples have passed by, the operation can give an instantaneous output. Morphological filtering can thus be used as a real time application, although it is to be noted that the output set generated by dilation is M−1 samples shorter than the data set, because the first M−1 output samples cannot be defined.

Figure 3A:
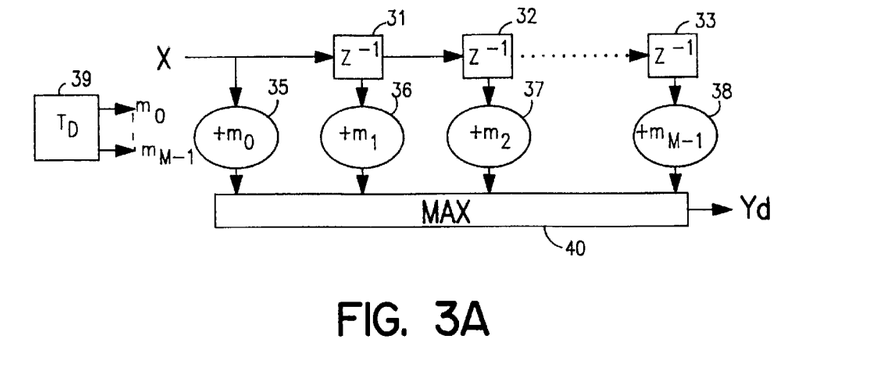
FIG. 3A is a schematic representation of a morphological dilation operation.

Referring to FIG. 3A, the input signal is shown as X, which is passed through successive delays 31, 32, . . . 33 as illustrated. Thus, when the first M−1 samples have been clocked through to taps 31–33, the first M samples are operated on by the addition operations as indicated. The values of $m_0, m_1, m_2 \ldots m_{M-1}$ are provided by the dilation template, indicated at 39. In a simple case, the additions may simply be +0. Block 40 is a maximum circuit, which selects the input which has the maximum value, and provides this max value as the sample output. Thus, the maximum value of $X_{n-i} + m_i$ is outputted for each value of n, producing the sample set Yd. It can be seen that the dilation produces a set which is M−1 samples shorter than the data set, because the first M−1 output samples cannot be defined.

The erosion of a function X (length N) by a template m with template length M, (Ye), is defined as:

$$Ye_n = E(X_n) = \text{MIN}_{i=0 \ldots M-1} \{X_{n+i} - m_i\} \quad O \leq n \leq N-M$$

Figure 3B:
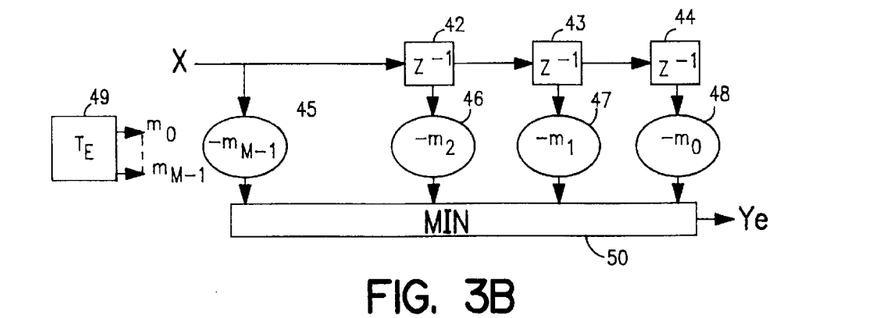
FIG. 3B is a schematic representation of a morphological erosion operation.
Figure 3C:
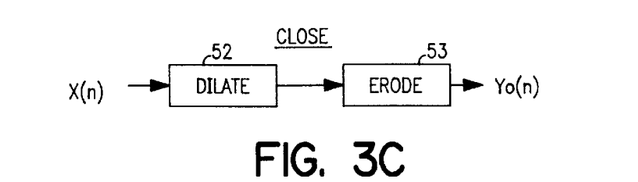
FIG. 3C shows a close operation, comprising a dilate operation followed by an erode operation.
Figure 3D:
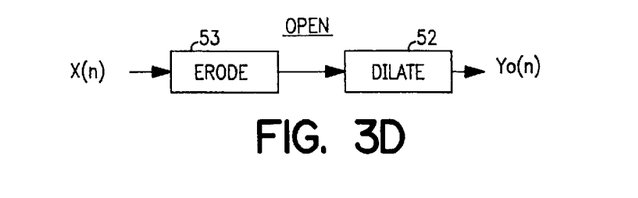
FIG. 3D shows an open operation, comprising an erode operation followed by a dilate operation.
Figure 3E:
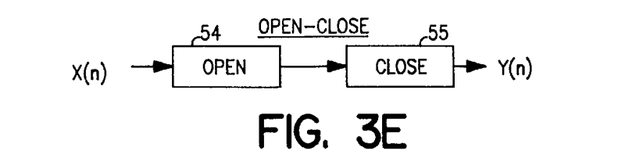
FIG. 3E shows an open-close operation comprising an open operation followed by a close operation.

The erosion operation subtracts, and thus is a shrinking operation, meaning that the outputs are always smaller than the inputs if the template $m_i$ is greater than zero for all i. As opposed to the dilation operation, erosion looks ahead in time, as seen by $X_{n+i}$. Therefore, in a real time application, the erosion circuit must wait until these future samples have passed by, thus causing a delay of M−1 samples, as shown in FIG. 3B. Also, as with dilation, an erosion operation generates an output set M−1 samples shorter than the data set, the difference being that the samples are lost at the end of the set. The input X, which can be provided by connecting the output Yd from the dilate circuit of FIG. 3A, is clocked into the respective taps 42, 43, 44. The subtractions are performed for each sample, by subtractor circuits 45, 46, 47, 48, having m respective template values determined by the erosion template data $T_E$ stored as indicated at 49. Circuit 50 examines the results of the subtraction operations, and outputs the minimum sample for each value of n, yielding $Y_e$. As discussed above, and for reasons made clear by the following illustrations, dilation and erosions are generally combined into filters known respectively as open and close filters. As illustrated in FIG. 3C, a close is made up of a dilate circuit 52 followed by an erode circuit 53. As illustrated in FIG. 3D, an open is made up of an erode 53 followed by a dilate circuit 52. Because a dilation and an erosion are combined in either an open or a close, the first M−1 samples are lost by the dilation and the last M−1 samples by the erosion, such that the output set generated by an open or close is 2(M−1) samples shorter than the data set. When constructing either an open or close filter from a dilation and an erosion, both operators can use the same template; however, the template data connected for the erosion operation is the reverse of that for the dilate operation, as can be seen from the equations and from a comparison of FIGS. 3A and FIGS. 3B. FIG. 3E illustrates an open-close circuit, being an open filter 54 followed by a close filter 55.

Figure 4A:
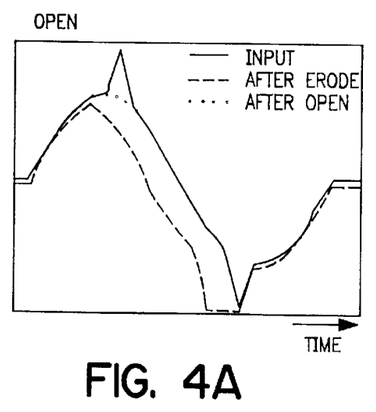
FIG. 4A shows the effect of an open operation in suppressing peaks, illustrating the signal after erode and also after dilate.
Figure 4B:
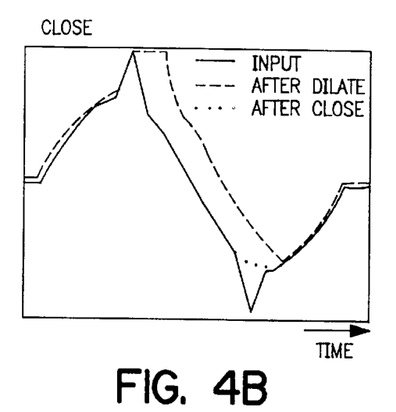
FIG. 4B shows the effect of a close operation in suppressing pits, showing the signal after dilate and after erode.

The result of opening a data sequence with a flat, or equal valued template, is that all peaks shorter than M−1 samples are eliminated. When closing the same sequence with the same template, all pits shorter than M−1 samples are eliminated. Therefore, an open is generally used to eliminate peaks, and a close is used to eliminate pits. These results are illustrated in FIGS. 4A and 4B. FIG. 4A shows the response of an open, i.e., an erode and then a dilate, with a template length, M of three samples, and m values of 1. After the erode operation, the peak has been suppressed from the output signal, but the pit has been lengthened. Following the dilate operation, the peak remains suppressed but the pit has been returned to its original position, such that the effect of the operation has been simply to suppress the peak which is less than the three samples. FIG. 4B shows the close operation, wherein the dilate operation first suppresses the pit but extends the peak, following which the erode operation returns the peak to its normal form, with the result being simply that the pit has been suppressed. Thus, in both open and close, the first step does the filtering of the either the pit or the peak, whereas the second step substantially recreates the original form of the input signal without the suppressed peak or pit.

Figure 4C:
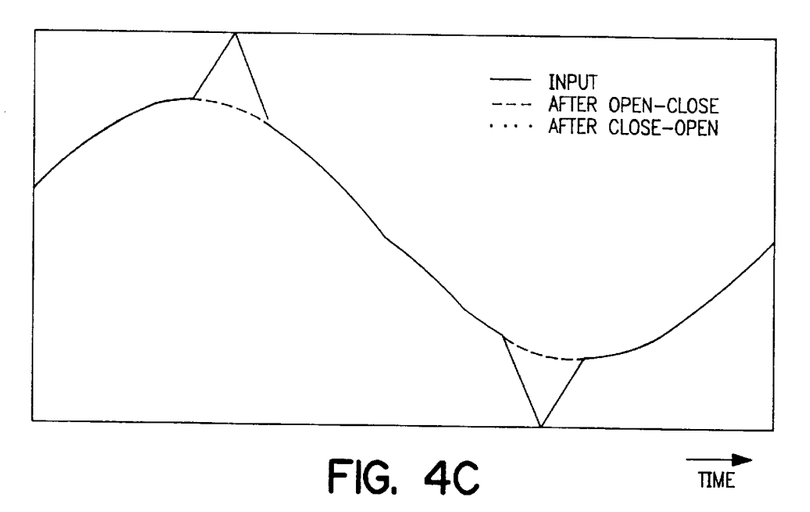
FIG. 4C shows a signal with both peaks and pits suppressed after either an open-close operation or a close-open operation.

When the open and close operations are combined, the two characteristics provide a filter that substantially suppresses both peaks and pits, while leaving the remainder of the signal unaffected. These filters are simply called openclose, e.g., first opening and then closing a signal, or close-open. An open-close is illustrated in FIG. 3E, where an open filter 54 is followed by a close filter 55. Since two dilations and two erosions are performed, the resulting output set has lost 2 (M−1) samples at the beginning and 2 (M−1) at the end, such that the output set is 4 (M−1) samples shorter than the previous set. The results for an open-close or close-open operation are shown in FIG. 4C, illustrating that both open-close and close-open achieve substantially identical results, eliminating the peak and pit. However, for a less ideal data set, bigger differences between the outputs of open-close and close-open may occur, especially for non-flat templates. It can happen where the first step stretches a peak or a pit beyond template length, thus making it impossible for the second to eliminate it. Thus, for a filter that is to primarily eliminate peaks, such as discussed below for use in rejecting FFR-waves from an AEGM, the use of an open-close is advisable, because the first step is better suited for this action.

For the preferred pacemaker embodiment of this invention, both size and energy consumption of the circuit must be minimized as much as possible, in order to preserve battery power. Consequently, the presently preferred embodiment embraces an analog form of morphological filters, with each dilate or erode unit requiring an analog delay line with M taps; an adder for every tap; a memory cell for each adder which is individually programmed; and a connection from each adder to the maximum or minimum circuit. In view of the fact that an extra memory cell per tap is needed, if the template values are variable, this suggests the desirability of using common template values, as otherwise the circuit complexity is at least linearly dependent on the template length; and further the circuit space and the required power consumption are increased with template variability. It has been found that, for processing the AEGM, the common template values (m) can be used without sacrifice of reliability. Of course, for more complex wave forms, variable templates may be required in order to achieve an optimum compromise of accurate filtering and cost. Also, to minimize the complexity of the calculations, and depending on the characteristics of the input signal, certain taps can be left out if the associated template values are small compared to adjacent values. When the rate of change of the input signal is limited that a small template value might be associated with the winner, i.e., either maximum or minimum, is small.

Figure 5:
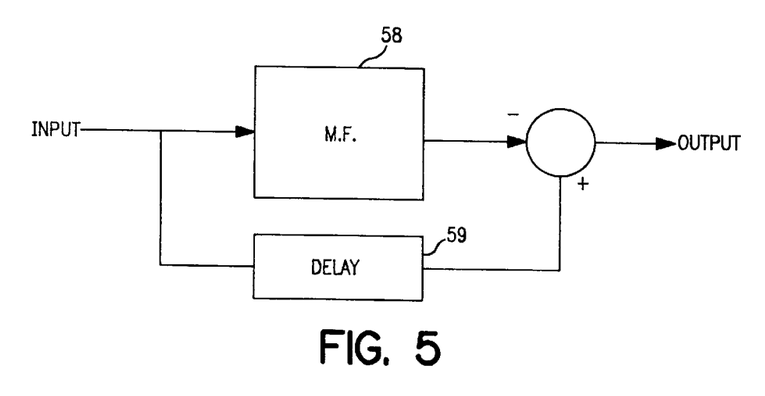
FIG. 5 is a circuit diagram illustrating the preferred arrangement of this invention for providing P-wave peaks while filtering FFR-wave portions from an AEGM signal.
Figure 6A:
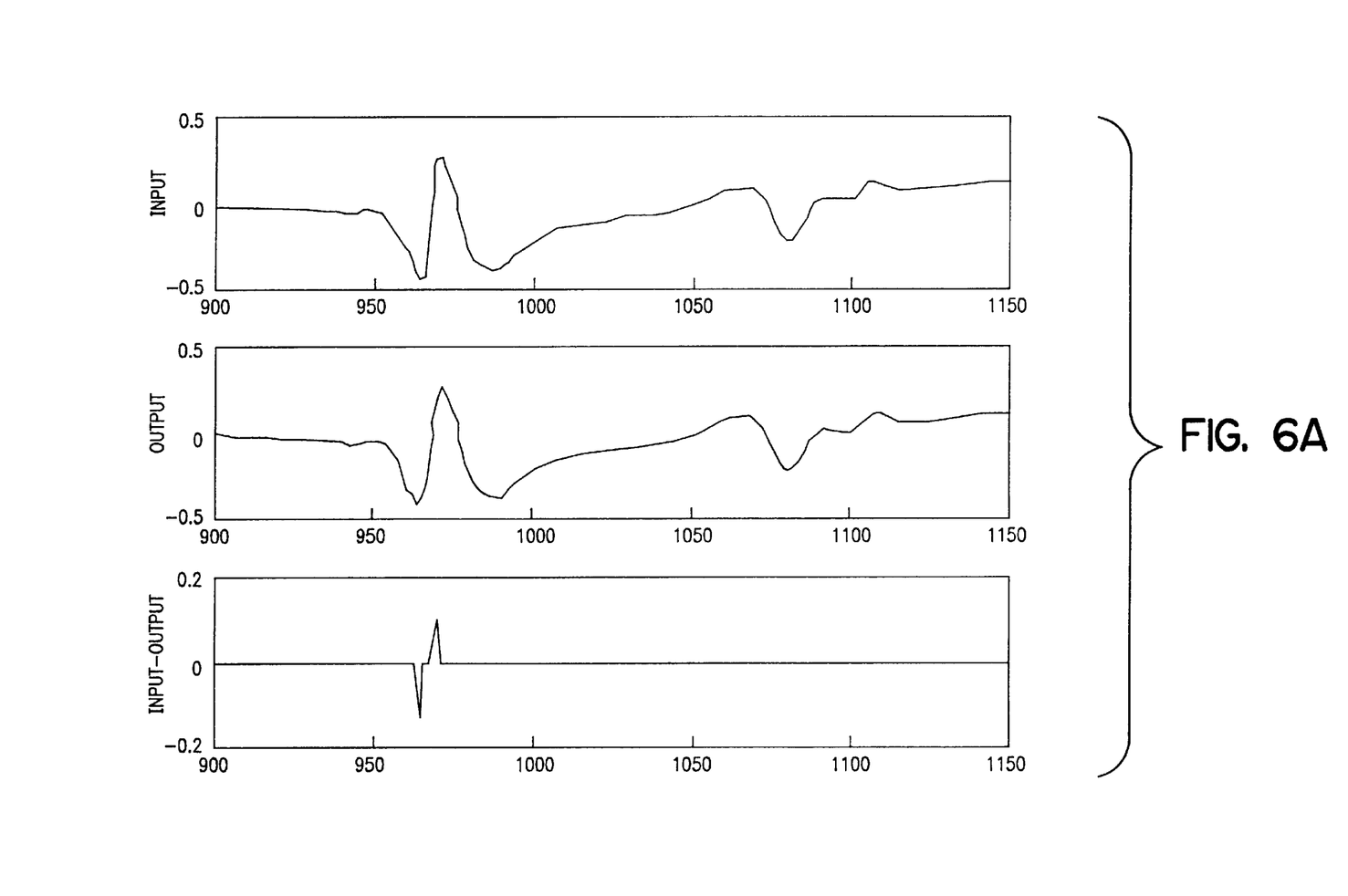
FIGS. 6A, 6B and 6C are sets of curves for M=3, 7 and 15 respectively, which illustrate the effect of the chosen value of M in the circuit of FIG. 5 for providing an optimum P-wave peak without any FFR-wave.
Figure 6B:
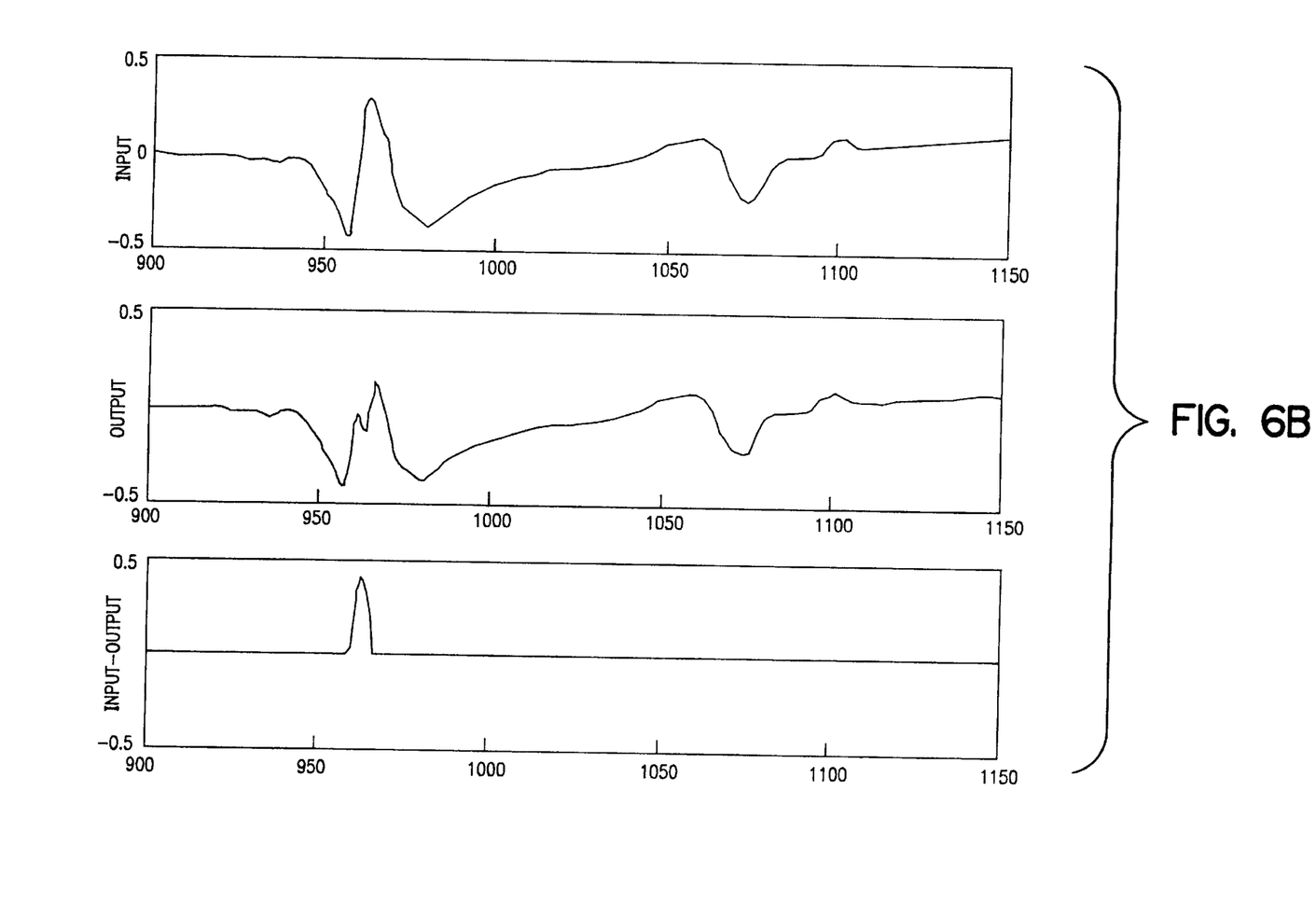
Figure 6C:
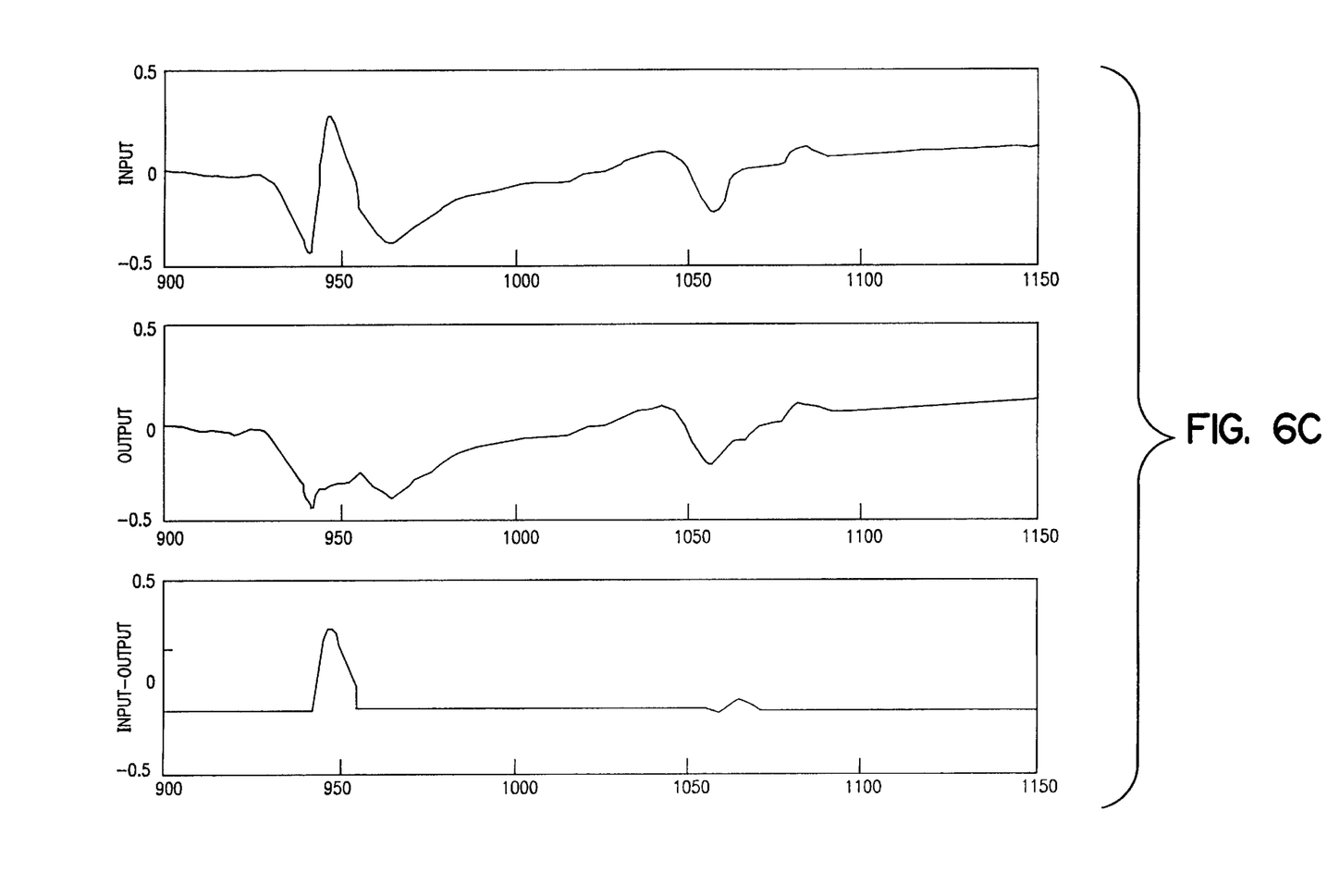

Referring now to the specific problem of capturing the P wave while rejecting the FFR-wave, it is important to recognize that the P wave is shorter in width, or duration than the FFR-wave. In order to filter out the FFR-wave with a morphological filter, it would be required to have a non-flat template with a length approximately the length of one AEGM period, i.e., one P-P interval. However, it is noted that the P wave itself can be suppressed with a template no larger than the length of the P wave, i.e., with a smaller template. Accordingly, the circuit of FIG. 5 is preferred, wherein the AEGM analog signal is inputted into morphological filter 58, which is set to suppress the P wave. The output, namely the input signal less the P wave peak which the pacemaker wants to see, is subtracted from the input signal, leaving only the P wave. The subtraction must involve signals that correspond in time, and since filter 58 introduces a delay, the input is passed through delay circuit 59 to introduce a like delay. The results of this operation, as well as the influence of the choice of M, is seen in FIGS. 6A, 6B and 6C. In FIG. 6A, a template length of three samples, with a clock frequency of 1 kHz, is utilized. As seen in the top curve, the input contains the larger amplitude P wave complex, as well as the FFR-wave. The output of the filter, with a portion of the positive going peak of the P wave subtracted, is different only in the area of the P wave. Consequently, as seen in the bottom curve, the input minus the output results in two peaks occurring around the P wave, one negative and one positive, both of these being three samples long. In FIG. 6B, a template of 7 samples length is utilized, resulting in a final output of just a positive peak which is 7 samples long. This appears to be an optimum result, because the positive P wave peak is clearly defined, and no FFR-wave is present. Note also that there is a clear zero baseline as a result of this operation. In FIG. 6C, a 15 sample long filter generates a larger peak around the P wave, but also yields a small response around the FFR-wave. While, in this specific case, the difference in amplitudes might be used to distinguish the two responses, this is clearly less desirable than the result of FIG. 6B. Additionally the longer template entails more expense and power consumption. Accordingly, the filter with M=7 is chosen as the best tradeoff between output amplitude and circuit complexity. As a general guide, the invention thus directs setting the template to a size compared to the wave portion of interest, so as to yield a clear peak output corresponding to the wave portion.

Figure 7:
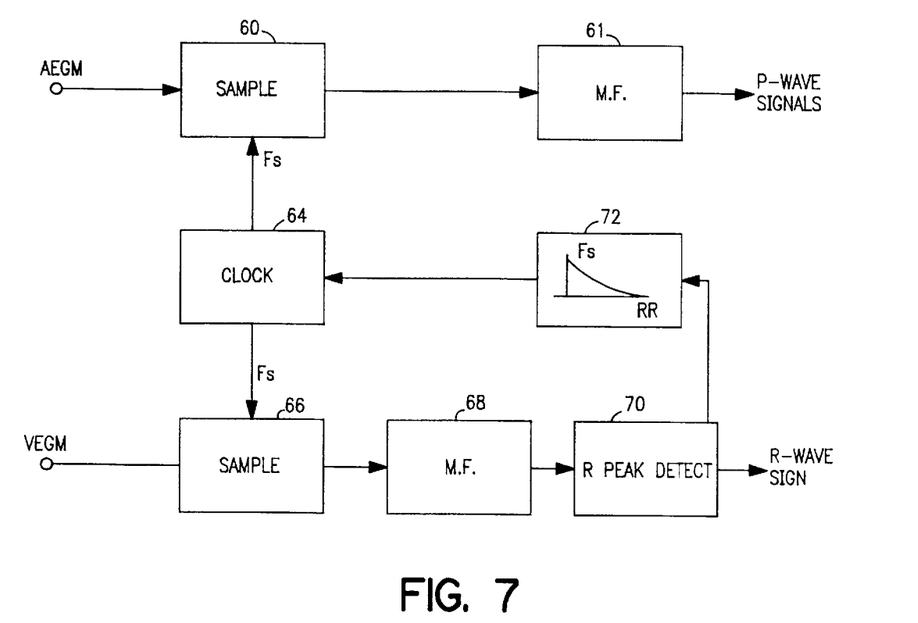
FIG. 7 is a circuit block diagram showing the manner of automatically adjusting the sample frequency for maintaining optimized filtering conditions as a function of cardiac rate variations.

Referring now to FIG. 7, there is shown a block diagram of a dual chamber pacemaker wherein the clock frequency, $F_S$ is adjusted to track variations in the rate of the cardiac signals. As shown, the atrial signal, or AEGM, is inputted into sample block 60, which is sampled by clocks generated at a rate $F_S$ by clock circuit 64. At the same time, the ventricular signal derived from the ventricular lead, or VEGM, is sampled at circuit 66, also by clocks at a rate of $F_S$. The AEGM samples are inputted into morphological filter 61, for deriving P wave signals; the VEGM samples are inputted into morphological filter 68 for deriving R-wave signals. The R-wave signals are also passed into peak detector 70, to provide R-wave pulses. The R-wave pulses in turn are inputted into circuit 72, which determines the RR rate, and provides an output control signal which corresponds to the RR rate. Thus, RR variations produce variations in QRS and P wave duration, and the pacemaker adapts by changing the sampling rate accordingly. The sampling rate control signal is connected from circuit 72 to clock circuit 64 in order to accomplish this automatic adjustment.

Figure 8:
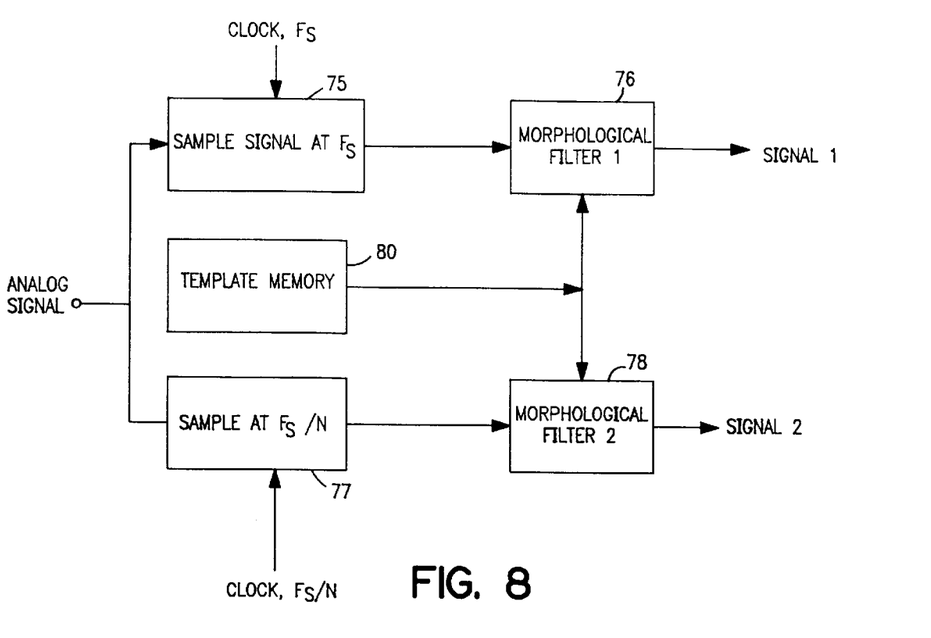
FIG. 8 is a circuit block diagram illustrating the use of plural morphological filters for operating on different signal portions.

Referring now to FIG. 8, there is shown a block diagram of a pacemaker, or like device for processing different portions of a signal, or different signals. Thus, in a typical pacemaker application, there may be a first morphological filter for separating out the QRS portion and a second for the T-wave portion; or there may be one morphological filter for separating out the QRS portion of the ventricular signal and another for the P-wave portion of the atrial signal. In such situations, the same template may be used for each morphological filter, with corresponding respective differences in the sample frequency for optimizing the signals which are to be filtered out. As illustrated in FIG. 8, a common analog signal is connected to sample circuits 75 and 77, which provide samples to filters 76 and 78 respectively. Sample circuit 75 is clocked with clock frequency $F_S$, whereas circuit 77 is clocked with clock signals at a frequency $F_S \div N$, where N may be any chosen number. In the illustrated embodiment, a common template is derived from memory 80, and inputted into both of the filters. Although not shown, memory 80 may be programmable by programming from an external source. In another embodiment, n different templates are used to control n different morphological filters, for identifying n respective wave types.

Figure 9:
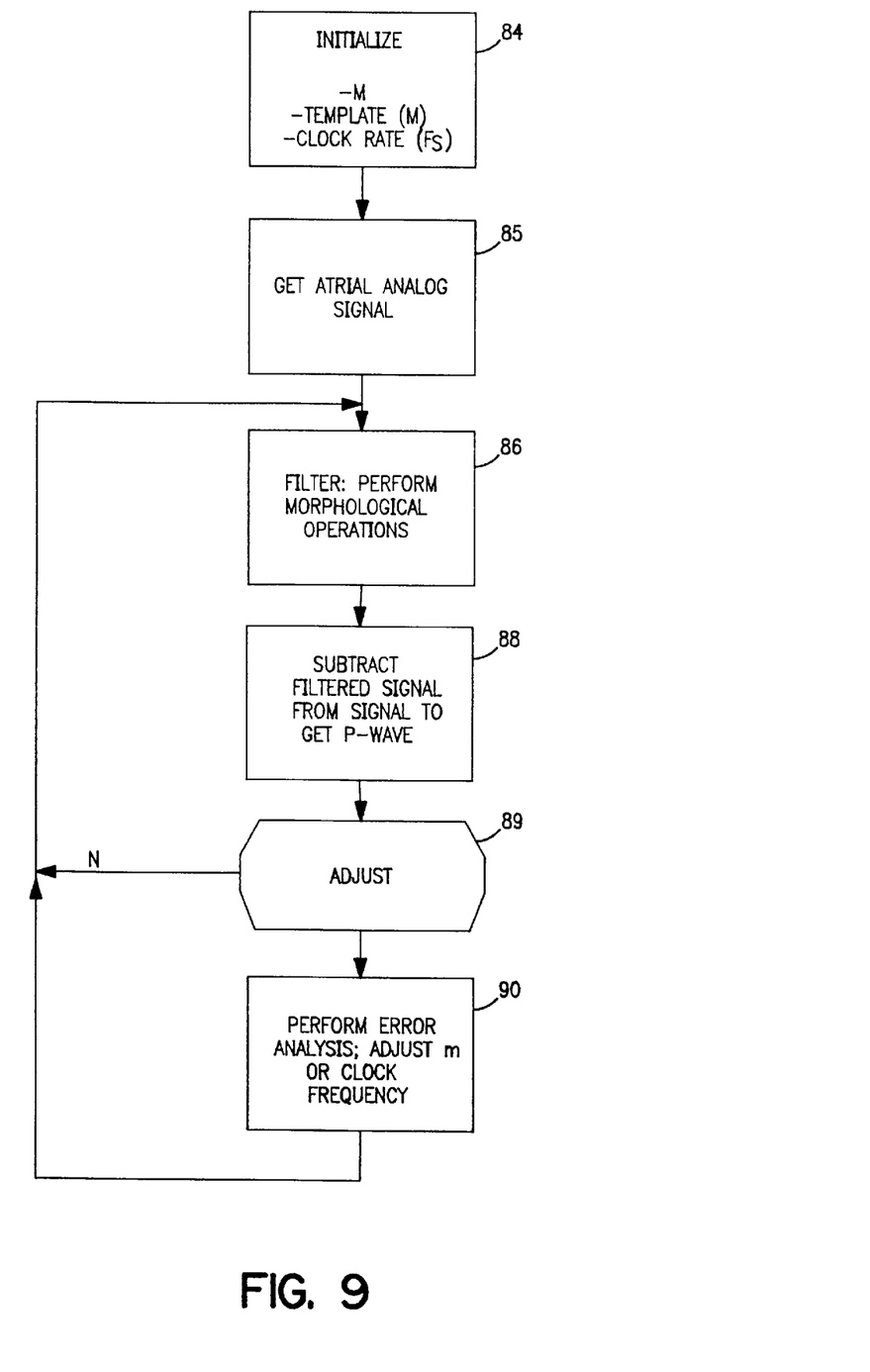
FIG. 9 is a simplified flow diagram illustrating the method of this invention for carrying out morphological operations on the AEGM to provide P-waves and to filter out FFR-waves.

Referring now to FIG. 9, there is shown a flow diagram which illustrates the primary steps taken in filtering signals in accordance with this invention, and for adjusting the template characteristics for the morphological operation. FIG. 9 specifically illustrates the steps taken in a pacemaker for deriving a P-wave from which the FFR wave has been suppressed. At 84, the length M of the operation; the template (m) numbers; and the clock rate ($F_S$) are initialized, in accordance with programmed initial data. At 85, the pacemaker gets a continuous atrial analog signal from the atrial lead, and provides it to the morphological filter. At 86, a filter performs the morphological operations, deriving a signal from which the P-wave has been removed, as discussed above. At 88, the filtered signal is subtracted from the analog signal to get the resultant P-wave peak signal. At 89, a decision is made as to whether to adjust the template length, the template or the clock frequency. If yes, at 90 the pacemaker performs an error analysis on stored values of recent P-waves, and prescribes a corresponding adjustment. Such an error analysis may suitably include evaluating variations in the root mean square of recent P-waves as detected. The routine then loops back and continues to perform the morphological operations on the incoming atrial signal.

Although the important application of sensing P-waves and filtering out FFR-waves has been illustrated, the invention is equally applicable for other pacemaker functions. For example, in an AAI pacemaker, it can be extremely useful to sense, i.e., pick out FFR-waves, so as to enable detection of ventricular depolarizations without a lead in the ventricle. This can be done by adjusting the template to the morphology of the FFR-wave. Here, the template width must be comparable to the FFR-wave length. Thus, the operation is the same as presented in FIG. 9, except that at step 88, it is the FFR-wave that is obtained. Likewise, different tachycardias can be discriminated by having respective morphological filters adapted to the shape of the tachycardia, e.g., a supra-ventricular tachycardia (SVT) can be discriminated from ventricular tachycardia (VT), and SVT can be discriminated from sinus tachycardia.

I claim:

1. A cardiac pacemaker which utilizes sensed P-waves for control of pacing operation, the cardiac pacemaker further having P-wave sense means operative cyclically, said P-wave sense means comprising:

signal means for obtaining an atrial signal from the patient's atrium;

sampling means for providing a sampled atrial signal;

morphological filter means for filtering out the P-wave portion from said sampled atrial signal to obtain a residual signal without said P-wave portion; and subtracting means for subtracting said residual signal from said sampled signal to obtain a P-wave signal without any substantial FFR-wave portion, and means for providing electrical stimulation to a patient's heart.

2. The pacemaker system as described in claim 1, wherein said morphological filter means comprises analog circuits.

3. The pacemaker as described in claim 1, wherein said morphological filter has an M of 5–10, and a sample rate within about 10 percent of 1 kHz.

4. The pacemaker as described in claim 3, wherein said morphological filter provides an effective operational length of about the duration of the patient's P-wave peak.

5. The pacemaker as described in claim 1, wherein said morphological filter has a template with M m values, and all said m values are equal.

6. The pacemaker as described in claim 5, wherein said m values are zeros.

7. The pacemaker as described in claim 5, wherein said morphological filter comprises an open-close filter.

8. The pacemaker as described in claim 5, wherein said morphological filter comprises an open filter.

9. The pacemaker as described in claim 1, comprising a second morphological filter, and a common template for said morphological filter and said second morphological filter.

10. The pacemaker as described in claim 9, wherein said morphological filter means comprises a first clock source for providing a clock pulses at a first frequency and said second morphological filter comprises a second clock source for providing clock signals at a second frequency.

11. The pacemaker as described in claim 1, wherein said morphological filter comprises a variable template, and template means for varying said template.

12. The pacemaker as described in claim 1, comprising a template, means for accumulating data representative of said P-wave signals and adjust means for adjusting said template as a function of said accumulated data.

13. The pacemaker as described in claim 1, wherein said template, has an operational length corresponding to a peak portion of the patient's P-wave.

14. The pacemaker as described in claim 1, comprising adjustable clock source means for clocking said sampling means, means for accumulating rate data concerning the patient's heartbeat, and adjust means for adjusting said clock source rate as a function of said accumulated data.

15. The pacemaker as described in claim 1, wherein said subtracting means comprises a delay circuit for delaying said sample signal before said residual signal is subtracted from it.

16. An implantable pacemaker for delivering pace pulses to the patient's heart, said pacemaker having sensing means for sensing atrial signals from said patient and control means for controlling pace pulse delivery as a function of sensed P-waves, comprising:

sample means for sampling said atrial signal to provide sample pulses representative of said atrial signal; and filter means for filtering said sampled signal to provide P-wave signals representative of P-waves pulses contained within said atrial signal, said filter comprising a morphological filter with an M width of at least about the duration the peak of said P-waves pulses.

17. The pacemaker as described in claim 16, wherein said filter comprises delay means for delaying said sampled signal, and subtract means for subtracting the output of said morphological filter from said delayed sampled signal, providing an output representative of said P-waves pulses.

18. A cardiac pacemaker having pulse generator means for delivering pace pulses to a patient's heart, sensing means for sensing atrial and ventricular cardiac signals from said patient's heart, and control means for controlling said pulse generator as a function of said sensed signals, said sensing means comprising:

atrial sensing means for obtaining a P-wave portion of each atrial wave when a P-wave occurs, said atrial sensing means further comprising a first morphological filter circuit for capturing a peak portion of each said P-wave;

ventricular sensing means for sensing at least one selected portion of the ventricular signal, said ventricular sensing means comprising a second morphological filter circuit for separating out a peak portion of said selected portion each time that it occurs; and template means for controlling each of said first and second morphological filters.

19. The pacemaker as described in claim 18, wherein said template means comprises a common template for each of said morphological filters circuits.

20. The pacemaker as described in claim 18, comprising adjustable clock means for providing clock signals to each of said first and second filters circuits, and adjusting means for sensing patient cardiac rate and for adjusting the rate of said clock signals as a function of said patient cardiac rate.

21. The pacemaker as described in claim 18, wherein said second filter comprises a filter for separating out peaks of patient R-waves.

22. A cardiac pacemaker having stimulus means for delivering stimulus pulses to a patient's heart, comprising;

atrial sensing means having an electrode adapted to be positioned in an atrial chamber of said patient for obtaining atrial signals, a first morphological filter for identifying FFR-wave portions of said signals, and a second morphological filter for identifying P-wave portions of said atrial signals.

23. A cardiac pacemaker comprising stimulus means for delivering stimulus pulses to a patient's heart, sensing means for sensing cardiac signals from at least one chamber of said patient's heart, and a plurality of morphological filters, each of said filters being connected to receive said cardiac signals and having a template adapted to discriminate a respective feature of said cardiac signals.

24. The pacemaker as described in claim 23, wherein at least two of said filters have common templates.

25. The pacemaker as described in claim 23, comprising a source of clock signals at a predetermined rate $F_S$, and clock means for connecting to each of said filters clock signals at a rate $F_S/n$, where n is selected for each respective filter.

26. The pacemaker as described in claim 23, wherein said sensing means comprises ventricular sensing means for sensing signals from a ventricular chamber of said patient's heart, and comprising a first of said filters which has a template matched to VT and a second of said filters which has a template matched to SVT.

27. The pacemaker as described in claim 26, wherein said sensing means further comprises atrial sensing means for sensing signals from an atrial chamber of said patient's heart, and comprising a third of said filters which has a template matched to sensed P-waves.

28. The pacemaker as described in claim 27, comprising a fourth of said filters which has a template matched to sensed FFR-waves.

29. The pacemaker as described in claim 23, comprising a morphological filter having a template matched to sensed T-wave portions of said signals.

30. The pacemaker as described in claim 23, comprising clock means for delivering clock pulses to said filters, and adjust means for adjusting the rates of said clock pulses as a function of the patient's cardiac rate.

31. An implantable medical device which senses P-waves, the device having P-wave sense means operative cyclically, the P-wave sense means comprising:

signal means for obtaining an atrial signal from the patient's atrium;

sampling means for providing a sampled atrial signal;

morphological-type filter means for filtering out the P-wave portion from the sampled atrial signal to obtain a residual signal without the P-wave portion, the morphological-type filter comprising an open-close filter; and subtracting means for subtracting the residual signal from the sampled signal to obtain a P-wave signal without any substantial FFR-wave portion.

32. The device as described in claim 31, wherein the morphological-type filter has an M of 5–10, and a sample rate within about 10 percent of 1 kHz.

33. The device as described in claim 32, wherein the morphological-type filter provides an effective operational length of about the duration of the patient's P-wave peak.

34. The device as described in claim 31, wherein the morphological-type filter has a template with m values, and all the m values are equal.

35. The device as described in claim 34, wherein the m values are zeros.

36. The device as described in claim 31, comprising a second morphological-type filter, and a common template for the morphological-type filter and the second morphological-type filter.

37. The device as described in claim 36, wherein the morphological-type filter means comprises a first clock source for providing a clock pulses at a first frequency and the second morphological-type filter comprises a second clock source for providing clock signals at a second frequency.

38. The device as described in claim 31, wherein the morphological-type filter comprises a variable template, and template means for varying the template.

39. The device as described in claim 31, comprising a template, means for accumulating data representative of the P-wave signals and adjust means for adjusting the template as a function of the accumulated data.

40. The device as described in claim 31, wherein the template, has an operational length corresponding to a peak portion of the patient's P-wave.

41. The device as described in claim 31, comprising adjustable clock source means for clocking the sampling means, means for accumulating rate data concerning the patient's heartbeat, and adjust means for adjusting the clock source rate as a function of the accumulated data.

42. The device as described in claim 31, wherein the subtracting means comprises a delay circuit for delaying the sample signal before the residual signal is subtracted from it.

* * * * *